US011363980B2

(12) United States Patent
Dauguet et al.

(10) Patent No.: US 11,363,980 B2
(45) Date of Patent: Jun. 21, 2022

(54) DEVICE FOR MEASURING AND/OR STIMULATING BRAIN ACTIVITY

(71) Applicants: Julien Dauguet, Paris (FR); Mehdi Dutheil, Sceaux (FR)

(72) Inventors: Julien Dauguet, Paris (FR); Mehdi Dutheil, Sceaux (FR)

(73) Assignee: CONSCIOUS LABS SAS, Limoges (FR)

( * ) Notice: Subject to any disclaimer, the term of this patent is extended or adjusted under 35 U.S.C. 154(b) by 179 days.

(21) Appl. No.: 16/461,289

(22) PCT Filed: Nov. 15, 2017

(86) PCT No.: PCT/FR2017/053126
§ 371 (c)(1),
(2) Date: May 15, 2019

(87) PCT Pub. No.: WO2018/091823
PCT Pub. Date: May 24, 2018

(65) Prior Publication Data
US 2020/0060571 A1    Feb. 27, 2020

(30) Foreign Application Priority Data

Nov. 15, 2016 (FR) ...................................... 1661057

(51) Int. Cl.
*A61B 5/369* (2021.01)
*A61B 5/00* (2006.01)
(52) U.S. Cl.
CPC ............ *A61B 5/369* (2021.01); *A61B 5/6803* (2013.01); *A61B 5/6843* (2013.01); *A61B 2562/02* (2013.01); *A61B 2562/164* (2013.01)
(58) Field of Classification Search
CPC ... A61B 5/4064; A61B 5/6803; A61B 5/6814; A61B 5/369; A61B 5/0006; A61B 5/291;
(Continued)

(56) References Cited

U.S. PATENT DOCUMENTS 8,731,633 B2 * 5/2014 Asjes ...................... A61B 5/369
600/383
8,938,301 B2 * 1/2015 Hagedorn .............. A61B 5/291
607/45
(Continued)

FOREIGN PATENT DOCUMENTS

KR    20160060535 A    5/2016
WO    2016/070188 A1    5/2016
WO    2016/080804 A1    5/2016

OTHER PUBLICATIONS

Written Opinion of the International Searching Authority dated Feb. 20, 2018, issued in corresponding International Application No. PCT/FR2017/053126, filed Nov. 15, 2017, 8 pages.
(Continued)

*Primary Examiner* — Sean P Dougherty
*Assistant Examiner* — Jonathan E. Cooper
(74) *Attorney, Agent, or Firm* — Christensen O'Connor Johnson Kindness PLLC

(57) ABSTRACT

A device for measuring and/or stimulating a brain activity, preferably an EEG device, including a transmitter and/or detector for transmitting and/or detecting physiological signals produced by the brain of an individual, and a support for the transmitter and/or detector, wherein the support is configured to extend over the top of the individual's head, the support removably attachable to an accessory intended to be worn by the individual, on his or her head, such as an audio headset, the support being configured such that, when the device is worn by the individual, the transmitter and/or detector are held in substantially close contact with the individual's head by the accessory.

24 Claims, 5 Drawing Sheets

(58) Field of Classification Search
CPC ... A61B 5/31; A61B 2562/164; A61B 5/6843; A61B 2562/0209
See application file for complete search history.

(56) References Cited

U.S. PATENT DOCUMENTS

| | | | |
|---|---|---|---|
| 2012/0029379 A1 | 2/2012 | Sivadas | |
| 2015/0313496 A1 | 11/2015 | Connor | |
| 2016/0143554 A1* | 5/2016 | Lim | A61B 5/6803 |
| | | | 600/383 |
| 2016/0360990 A1* | 12/2016 | Altshuler | A61N 1/0456 |
| 2016/0367189 A1* | 12/2016 | Aimone | A61B 5/291 |
| 2019/0239763 A1* | 8/2019 | Block | A61B 5/377 |

OTHER PUBLICATIONS

International Preliminary Report on Patentability dated May 21, 2019, issued in corresponding International Application No. PCT/FR2017/053126, filed Nov. 15, 2017, 1 page.
International Search Report dated Feb. 20, 2018, issued in corresponding International Application No. PCT/FR2017/053126, filed Nov. 15, 2017, 3 pages.
Written Opinion of the International Searching Authority dated Feb. 20, 2018, issued in corresponding International Application No. PCT/FR2017/053126, filed Nov. 15, 2017, 7 pages.

\* cited by examiner

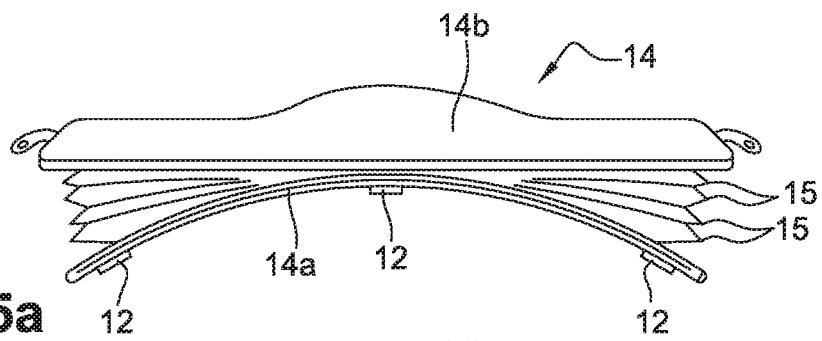
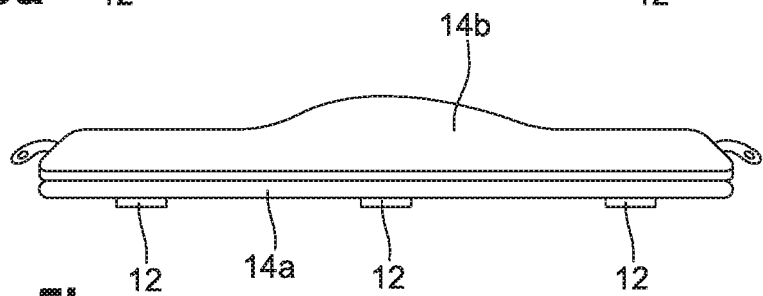
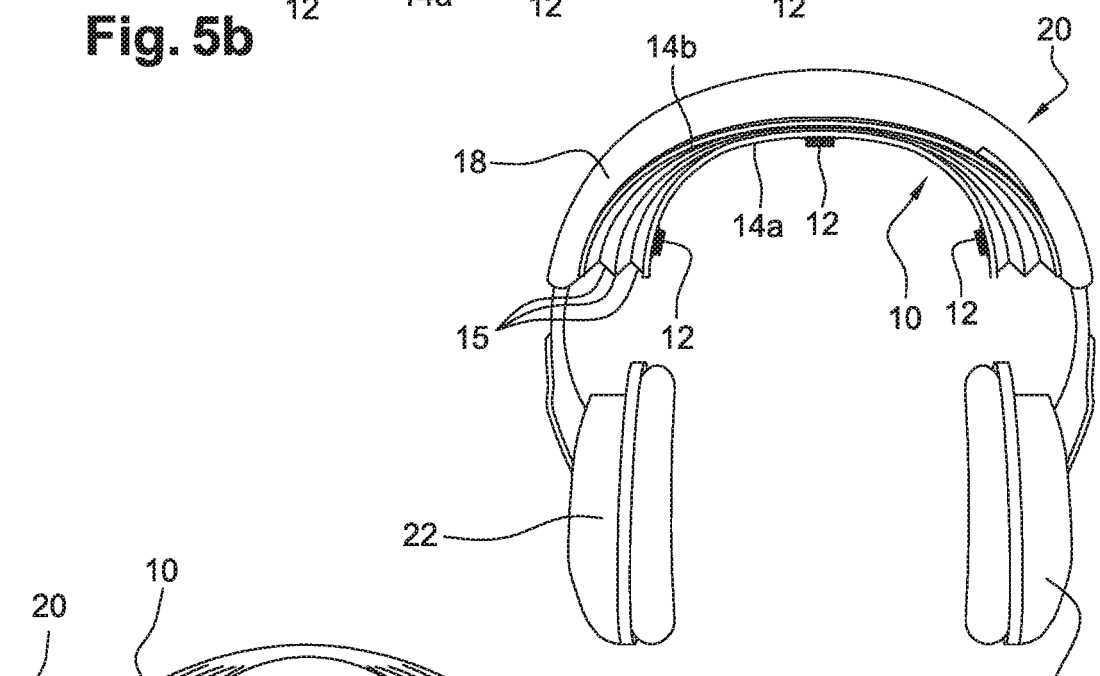
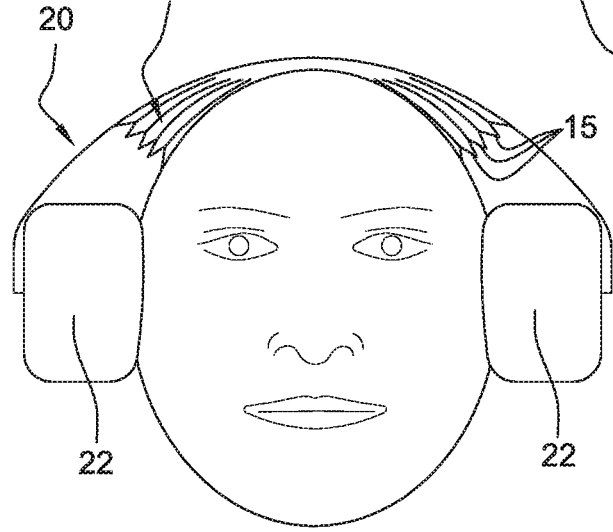
Fig. 5a
Fig. 5b
Fig. 6a
Fig. 6b

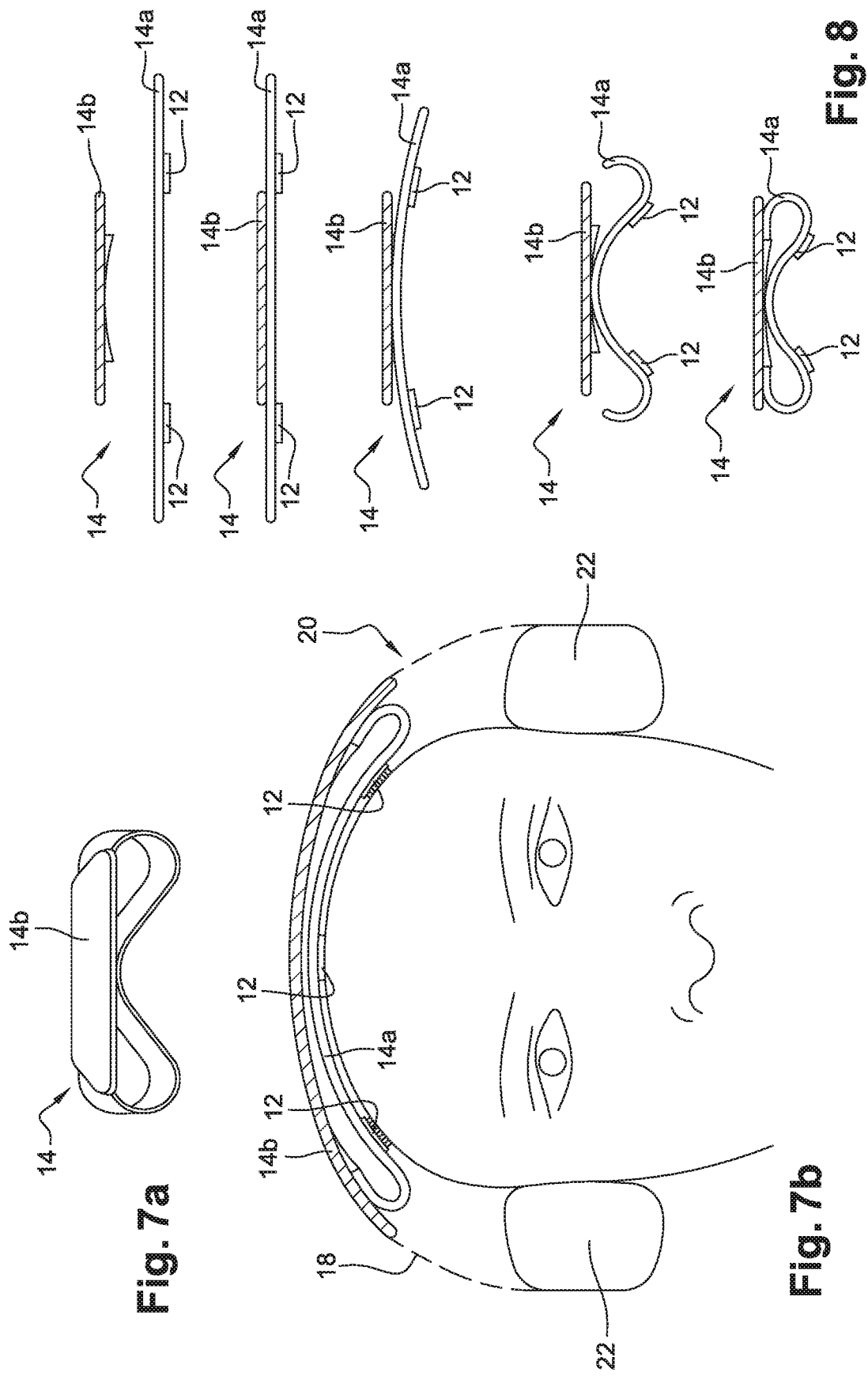

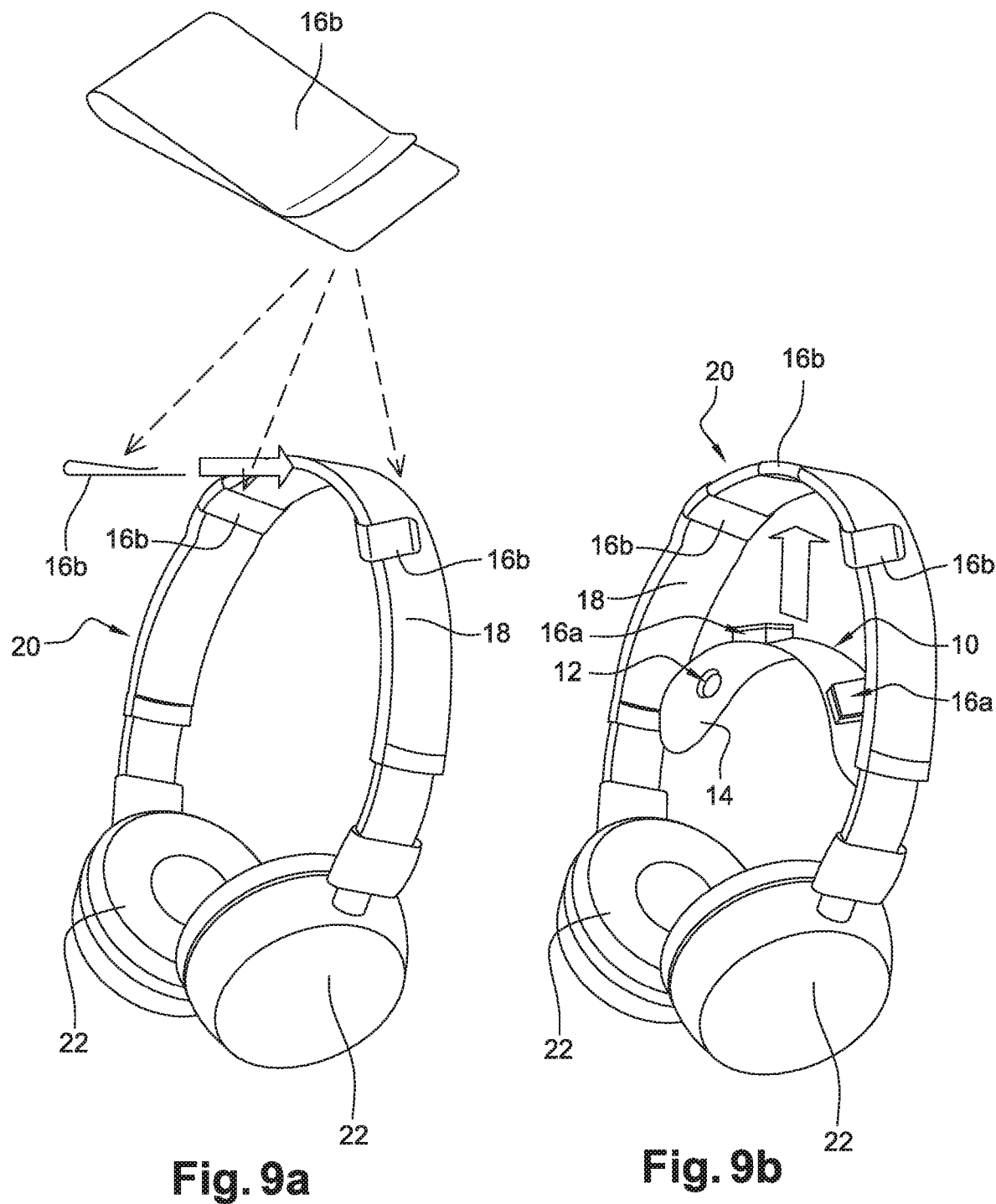

DEVICE FOR MEASURING AND/OR STIMULATING BRAIN ACTIVITY

TECHNICAL FIELD

This invention concerns a device for measuring and/or stimulating the brain activity of an individual (e.g. electric) or other types of bio-measurements such as pulse, and an audio headset equipped with such a device.

TECHNICAL BACKGROUND

There are various ways to measure a person's brain activity: BCT (Brain and Core Thermometer) thermal measurements, optical measurements (e.g. near infrared spectroscopic imaging (NIRS)), magnetic measurements (magneto-encephalography), etc.

A classic and well known way of measuring an individual's brain activity is to measure brain electrical activity. A device for measuring brain electrical activity (or electroencephalograph) makes it possible to monitor the global activity of large groups of neurons in the brain. The electroencephalogram (or EEG) is classically used in clinical practice for diagnostic purposes or in research for brain exploration. The EEG can be used to determine different states in an individual: state of consciousness, of waking, sleep stage, degree of cognitive engagement, stress level, etc. The amplitude of an electrical signal is proportional to the degree of synchronization of nerve activity of neurons in a given region of the cortex. Indeed, when a group of neurons is excited simultaneously, their weak transmitted signals add up and become perceptible for electrodes on the surface of the skull.

In the current technique, there are many devices of the electroencephalograph type. They each have sensors for detecting electrical signals transmitted by an individual's brain, and a support for these sensors. In a classic and well-known way, the general shape of an EEG helmet (invented at the beginning of the 20th century) used in medical or research circles is essentially that of a bonnet. Often, like ECG (electrocardiogram) devices on the heart, the electrodes of an EEG device are directly placed and individually glued one by one on the individual by a specialized technician, with adhesive conductive paste sometimes lined with a medical adhesive tape. The whole is then covered with a net. The EEG is a method of exploring the brain that includes a spatial, frequency and temporal component: it therefore involves having several electrodes distributed over the skull of the individual.

In order to preserve the space component, the EEG helmets used in research have a spider shape. However, the so-called "general public" EEG devices accessible to individuals for personal and private use generally operate by means of dry electrodes, the vast majority of which contain coplanar electrodes grouped together in a specific region such as the forehead. These "general public" devices are therefore classically presented in the form of a headband or in a general elongated and C or U curved to conform to the shape of the head of the individual wearing it, and the support extends over his forehead.

Other "general public" devices include sensors located on the top of the head of the wearer but their use is made inseparable from the use of the headset because of their integration with it, which is very impractical when the individual wishes to use only the headsets, or use the EEG with a different support. This makes the device difficult to handle and limits its use.

In addition to electrical measurement, there are other techniques for measuring an individual's brain activity that require the presence of a sensor in contact with (or near) the scalp. Examples include NIRS (Near Infra Red Spectroscopy) photonics, measurement of magnetic field produced by electric currents naturally flowing in the MEG brain (Magnetoencephalography), BCT (Brain Core Temperature) thermal measurement, or ultrasonic measurement, "Functional Ultrasound Imaging" (functional ultrasound imaging).

This invention proposes an improvement of these technologies in order, on the one hand, to reintroduce the space component into the measurements of EEG devices intended for the "general public" by giving in particular the possibility of reaching other brain regions (central, parietal, occipital, temporal region), while facilitating their use. On the other hand, this invention proposes to make other methods of measuring brain activity accessible to the "general public".

Apart from the techniques for measuring brain activity, there are techniques (in full expansion) for stimulating brain activity. These techniques are commonly referred to as neuromodulation, and are classically of the photonic, magnetic, ultrasonic and/or electrical type.

Cerebral photonic stimulation, or photo neuromodulation, is based on the fact that the absorption of photons causes photochemical reactions in an individual's neurons and alters their activity. The light source can be a "near infrared laser" or a light-transmitting diode. This stimulation technique can be LLLT (Low-level Light/Laser Therapy) types.

Non-invasive (or minimally invasive) brain magnetic stimulation is called TMS (Transcranial Magnetic Stimulation): this technique consists of generating a magnetic field through an antenna on the surface of the stimulated individual's brain. This will induce electrical micro-currents in the brain region under the antenna (electromagnetic induction principle).

The non-invasive (or minimally invasive) ultrasound brain stimulation technique can be of the TPU (Transcranial Pulsed Ultrasound) type: for example, it can use low-frequency, low-intensity ultrasound to modulate the brain activity of the stimulated individual, probably by generating mechanical action on cell membranes.

Cerebral electrical stimulation is presented classically, and in a manner known per se, in two forms:
- tDCS (Transcranial Direct Current Stimulation) direct current stimulation, and
- tACS (Transcranial Alternating Current Stimulation) alternating current stimulation.

The supposed mechanisms of action of cerebral electrical stimulation aim to depolarize/hyperpolarize (tDCS) neuron membranes or synchronize/desynchronize (tACS) the natural electrical oscillations of the stimulated individual's neurons in a cortical region.

All these stimulation techniques can be made available to the "general public".

The present invention thus proposes to democratize access to these brain stimulation techniques via a practical and easy-to-use device.

SUMMARY

The invention proposes for this purpose a device for measuring and/or stimulating a brain activity, preferably an EEG device, comprising means for transmitting and/or detecting physiological signals produced by the brain of an individual, and a support for said transmitting and/or detecting means, said support being configured to extend over the top of the individual's head, the support comprising means for removably attaching to an accessory intended to be worn by the individual, on its head, such as an audio headset, the support being configured so that the transmitting and/or detecting means are, when the device is disposed on the head of the individual, interposed between the accessory and the head of the individual, and maintained in substantially tight contact on the head of the individual, characterized in that the device is configured to operate autonomously.

This device makes it possible, in particular, to measure the cerebral state in which the individual finds himself in order to possibly adapt his direct electronic environment to this state or, conversely, to induce a particular cerebral state adapted to his environment or activity. The brain activity measured is advantageously the brain's electrical activity, the transmitting and/or detecting means including a sensor for detecting electrical signals.

The invention also makes it possible to stimulate brain activity to induce a certain brain state while measuring the brain activity of said individual. For example, the individual's brain can be stimulated by an optical signal transmitted from a transmitter, such as a diode, while an electrical sensor, such as an electrode, measures the individual's brain activity. This creates a feedback loop and secures possible brain stimulation.

According to the invention, the support is removably attached, i.e. removable and attachable (at will), to an accessory that is preferably chosen from an audio headset, for example with a hoop, a hair band, a pair of glasses, a protective helmet, a head gear, a cover, a bonnet, a cap, a hat, a headscarf, a headband, a wedge-style cap, a kippa, a virtual reality or augmented reality headset, augmented reality glasses, etc. This allows the device to be worn in addition to one of the above accessories without discomfort and can be dismantled and disassembled from the accessory.

Several options are then available to the individual who wishes to wear the device: If the autonomous device is long enough to enclose the individual's head, the device holds itself on the individual's head, i.e. it can be worn alone, without being attached to an accessory and without risk of being lost. However, the possibility of attaching it to an accessory remains. In the event that the device support is not able to hold by itself on the head of the individual, the device may be attached with one of the above accessories, in particular a hair band, to extend the support and carry it without risk of losing it.

The fact that the device is configured to operate autonomously, such that it can be used alone, in a fully operational electronically way. However, to ensure that it is held on the user's head, an accessory is required.

The device thus has an electronic autonomy, i.e. it has an electronic system (battery, analog-to-digital converter, microcontroller, wireless communication module, etc.) that is autonomous and independent of the head accessory to which it can be attached, such as a Bluetooth headset.

The device operates electronically in an autonomously manner, i.e. it is able to operate without using the electronics of the accessory. Some additional electronic features not essential for its autonomous operation (additional battery, memory, control buttons, etc.) may require a connection to the accessory.

The electronic autonomy allows the device to be independent of the electronics of the accessory to which it can be attached and thus to be compatible with several different accessories, such as a cap and audio headsets for example. This makes it possible to extend the measurement of brain activity over long periods of time by switching from one head support to another depending on the situation. For example, a person works at his or her desk with an audio headset to which the brain activity measuring device is attached. He/she then goes to a meeting and replaces the headset with a hair band accessory, then attaches the device to her motorcycle helmet to continue measuring the signal on her way home from work. All its measurements are carried out by the same device, potentially connected wirelessly to the same telephone or tablet type terminal.

Once attached to the accessory, the assembly formed by the device and the accessory can be placed and removed with a single movement.

The fact that the device is removable makes it possible to choose and adapt the accessory to which it is coupled according to the situation in which you wish to use the device and therefore to use it in different contexts, situations and places without risk of disturbing, surprising, annoying or offending those around you. For example, you can couple it with a cap to read in a park, a protective helmet to do work on a construction site or a bike ride, and couple it with an audio headset to concentrate in an open space. This allows, for the same device, an ease and flexibility of use essential for uses adapted to all kinds of daily activities. In addition, the same cap, protective helmet and audio headset can be used without being coupled to the device. Thus, a single device is sufficient to cover a huge range of activities and there is no need to add accessories "without devices" and "with devices" in your personal belongings. The decoupling between the device and the accessory thus allows a personalized combination: in terms of audio headsets, hats, construction site helmets, etc., the needs and choices can be very specific and personal. If the user is already equipped with an accessory that he has purchased independently of his wish to measure brain signals, and he wishes to keep the personal use of this accessory, for example for hygienic reasons, removability thus makes it possible to reconcile a pre-existing accessory with the device. The only constraint is to wear an accessory adapted to the use of the device in the event that the device is not autonomous.

In addition, the device may not be able to surround the head, it may be small in size and can be stored flat: this simplifies transport and storage.

The device can easily be declined in several sizes or shapes to best suit the user and use, independently of the fashion and currents that change the design of an audio headset or cap, for example.

In addition, if it is necessary to replace either the device or the accessory, it is not necessary to replace the whole but simply an individual element.

The invention proposes a particular positioning of the device on the head of the individual. Like a hair band, the device extends over the top and sides of the individual's skull, making it more discreet, comfortable, practical, functional and aesthetic than, for example, devices extending over the forehead.

The invention also proposes a device comprising means for transmitting and/or detecting physiological signals intended to be located under the accessory worn by the individual. This allows the accessory to exert pressure on the signal transmitting and/or detecting means and thus optimizes contact between the user's scalp and said signal transmitting and/or detecting means without creating inconvenience or discomfort.

The device according to the invention may include one or more of the following characteristics, taken in isolation from each other or in combination with each other:

electronic elements of the device are shared with the accessory, removable attaching means are integrated into the device, the removable attaching means are intended to be attached to the device, and can for example take the form of magnetic clip, the support has a general elongated shape curved in C or U, the support includes one or has a relatively thin strip shape configured to be interposed between the accessory and the individual's head, the support has a general shape of a headband, the support is made of flexible material, in order to adapt as best as possible to the curvature of the individual's head and/or the accessory worn by the individual, the support is articulated, so as to adapt as best as possible to the curvature of the individual's head and/or the accessory worn by the individual, the support consists of several sheets, so as to have a so-called closed position, in which it has the shape of a strap and an open position, in which it has the shape of a bellows, so as to adapt as well as possible to the shape of both the head of the individual and the shape of the accessory and to optimize contact between the means of transmitting and/or detecting physiological signals and the head of the individual, the support consists of two semi-rigid strips of different lengths, superimposed, attached to each other by their centers, the upper strip comprising means for attaching each of the ends of the lower strip in such a way as to present a so-called open position, in which the support has an overall shape of a strap and a closed position, in which the ends of the lower strip are folded and fixed to the upper strip via the attaching means, so as to have a spring loop shape in order to best adapt both the shape of the individual's head and the shape of the accessory to optimize contact between the means of transmitting and/or detecting physiological signals and the individual's head, the support comprises, substantially in its middle, i.e. at the top of the C or U, said attaching means, the support comprises at least two attaching means apart from each other, and preferably evenly distributed along said support, said attaching means form a loop which is intended to enclose said accessory or be traversed by said accessory, said connecting or attaching means are of the type of magnets, hooks and loops, shape cooperation, elastic clipping, anti-slip elements and/or elastic elements, said transmitting and/or detecting means are located on an inner face of said support, for example, concave curved, said transmitting and/or detecting means are in the form of pins or discs comprising at least one dry electrode configured to come into contact with the scalp of the individual wearing the device, without the use of coupling liquid, despite the presence, or not, of hair, the electrodes have protruding pimples whose free ends are configured to come into contact with the scalp of the individual wearing the device, without the use of coupling fluid, despite the presence, or not, of hair, the pins or discs are made of a conductive polymeric material, preferably soft or flexible, the device further includes at least one electronic board for amplifying the electrical signals detected by the sensors, and for processing said signals, at least one of said transmitting and/or detecting means is attached to a local amplification electronic board, at least one of said transmitting and/or detecting means is an optical sensor comprising a radiation source (e. g. LED light emitting diode), a detector (e. g. CMOS type), and a dispersive element (e. g. diffraction grating), at least one of said transmitting and/or detecting means is of the chip-scale atomic magnetometer (CSAM) sensor type intended for measuring magnetic fields. This type of sensor typically has the following characteristics: high sensitivity, low cost, no cooling required, low power consumption, portable, no need for direct contact, etc., at least one of said transmitting and/or detecting means is of the micro thermistor sensor type, allowing the brain temperature to be measured using, for example, the zero heat flow principle, at least one of said transmitting and/or detecting means is of the cerebral electrical stimulation electrode type, associated with a module capable of generating electrical micro-currents, at least one of said transmitting and/or detecting means is of the LED (Light Emitting Diode) type producing light stimulation in the near infrared spectrum (wavelength between 750 and 1400 nm), for example targeting the prefrontal cortex following ultra-short pulses at a frequency of 10 Hz, at least one of said transmitting and/or detecting means is of the conductive coil type (or butterfly coil pair), comprising a copper cable covered with insulation, of circular shape and diameter in the range of 2-10 cm, and producing a magnetic field, at least one of said transmitting and/or detecting means is of the piezoelectric transmitter or CMUT (Capacitive micromachined ultrasonic transducers) type capable of generating a low intensity low frequency ultrasonic wave of around 5-6 MHz for example, directed towards the individual's brain, the device also includes means for remote communication with an electronic system independent of said accessory, such as a mobile phone, the support is in the form of a hair band and is configured to enclose the individual's head from the top of his head to the vicinity of his ears, said transmitting and/or detecting means are removably attached on the support or this support includes removable and replaceable elements, at least one of the measurement and/or stimulation devices is positioned in contact or close to the scalp (out of the forehead) of the user. This extends the spatial component of the measurement or stimulation, and allows the device to be less sensitive to physiological artifacts such as eye or forehead movements of the user, the support is configured to pass under the accessory worn by the individual. This ensures that the transmitting and/or detecting means are properly maintained in contact with the user's scalp, and also makes it possible, when the device is worn by a user, to hide the transmitting and/or detecting means and thus protect them from any shocks that may damage them and thus reduce the operating time of the device, said transmitting and/or detecting means are configured to detect other types of bio measurements such as pulse.

The present invention also concerns an audio headset, comprising a hoop carrying in two opposite ends means for transmitting sounds or music, characterized in that it comprises at least one device as described above removable attached in particular to the support.

This invention also concerns a sensor for detecting signals, preferably electrical signals, transmitted by an individual's brain, in particular for a device for measuring cerebral electrical activity, preferably an EEG device, as described above, this sensor having one or more of the characteristics described above, taken in isolation from each other or in combination with each other.

DESCRIPTION OF THE DRAWINGS

The invention will be better understood and other details, characteristics and advantages of the invention will appear more clearly when reading the following description as a non-limitative example and with reference to the attached drawings in which:

FIGS. 5a and 5b are schematic views in perspective of a device support in a second embodiment, FIG. 6a is a schematic front view of the device according to the second embodiment, attached to an accessory, FIG. 6b is a schematic front view of the device according to the second embodiment, attached on an accessory and worn by an individual, FIG. 7a is a schematic view in perspective of the device according to a third embodiment, FIG. 7b is a schematic front view of the device according to the third embodiment, attached to an accessory and worn by an individual, FIG. 8 is a series of schematic views, from the front, of the device according to the third embodiment, showing the assembly of the device, FIGS. 9a and 9b represent the attachment of the device of FIG. 1 to an accessory, in an embodiment in which the removable attaching means are not integrated into the device, FIG. 11c is another schematic axial cross-sectional view of the sensor in FIG. 11a.

DETAILED DESCRIPTION

Figure 1:
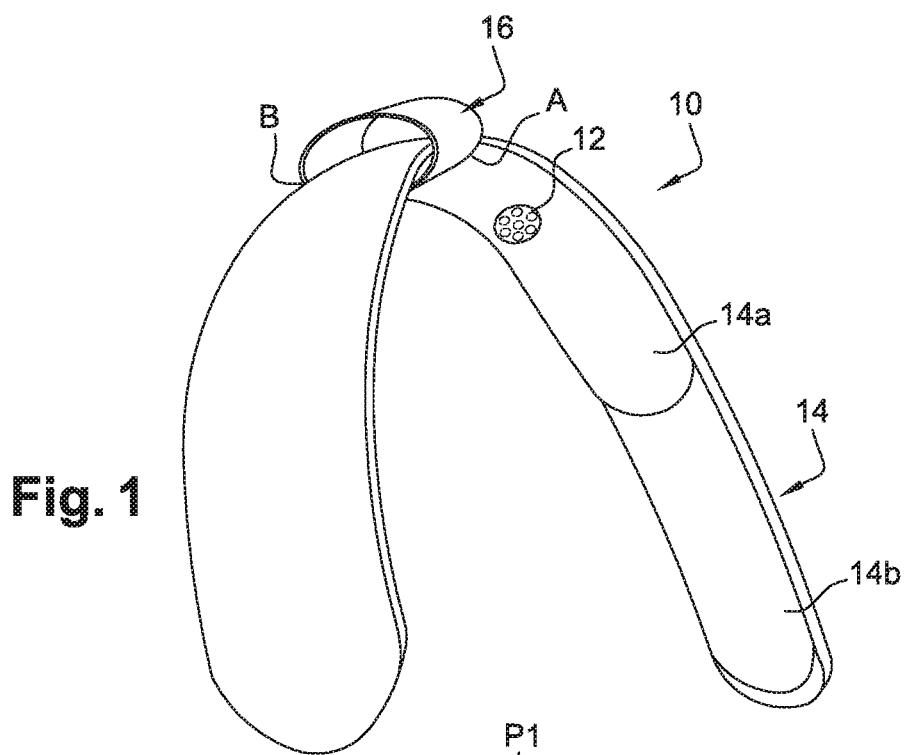
FIG. 1 is a schematic view in perspective of a device according to a first embodiment of the invention.
Figure 2:
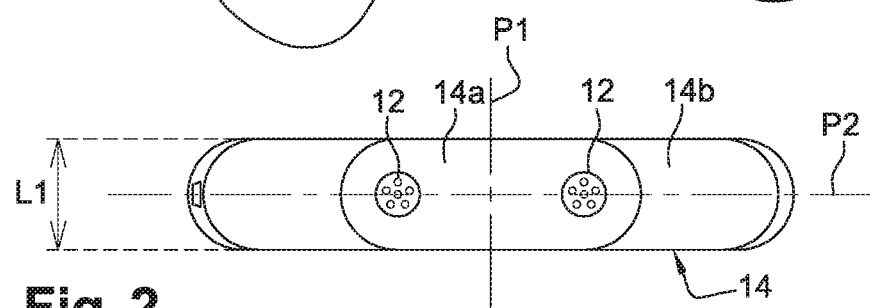
FIGS. 2 to 4 are other schematic views of the device of FIG. 1, seen from below, above and to the side respectively.
Figure 3:
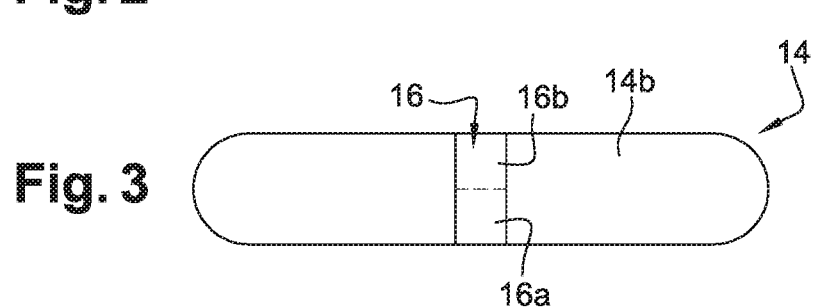
Figure 4:
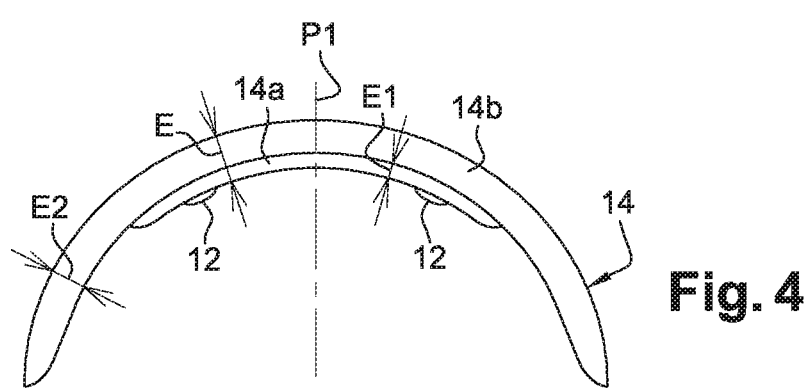

FIGS. 1 to 4 represent a first embodiment of a device 10 according to the invention of measuring an individual's brain activity. In this embodiment, the device 10 measures the electrical brain activity (EEG) of the individual who wears it.

According to this embodiment, the device 10 essentially includes:
- transmitting and/or detecting means 12, in this case sensors 12 for detecting electrical signals transmitted by the individual's brain,
- a support 14 for sensors 12, and
- means 16 for removably attaching the support to an accessory intended to be worn by the individual on his or her head, such as a headset (FIGS. 9a and 9b).

Figure 10A:
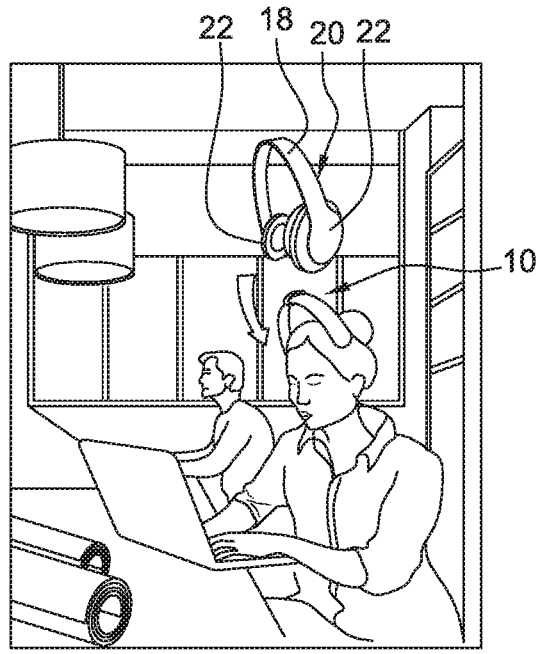
FIGS. 10a and 10b represent the positioning and fixing of the device in FIG. 1 on an individual's head, in a embodiment in which the removable attaching means are integrated into the device.

Sensors 12 will be described in detail in the following with reference to FIGS. 10a 10c.

In this embodiment, the support 14 has a generally elongated and C or U curved shape. It is configured to extend to the top or even the sides of the individual's head. It includes here two curved parts 14a, 14b mounted one inside the other, or superposed.

In an alternative manner, not shown, the support 14 may have a general shape of a headband, which allows some pressure to be exerted on the means 12 of transmitting and/or detecting physiological signals even in the absence of an accessory 20, thus allowing the sensors and/or transmitters 12 to be kept in contact with the user's skull. By headband, we mean any accessory 20 forming an O, worn around the head of an individual. The headband can, for example, pass over the forehead or top of the head of the wearer, pass in front or behind the ears, attach to the back of the head or under the chin, etc. The inner or lower part 14a is shorter than the outer or upper part 14b.

When worn, the outer part 14b extends over the head of the individual, at an angle between about 150 and 200°, and for example 10 of 180°. It thus extends globally over the top and sides of the individual's head, for example, to the vicinity of the top of the ears, in the manner of a hair band.

When worn, the inner part 14a extends over the head of the individual, at an angle between about 50 and 120°, and for example of 90-100°. It also extends globally to the top of the individual's head.

In the example shown, the function of part 14a is to support sensors 12 and integrate the acquisition circuit. The function of part 14b may include, but is not limited to, positioning and maintaining the device 10 on the individual's head.

Parts 14a, 14b can be fixed together in a removable manner. For example, the individual can customize the device by replacing part 14b with the same part but of a different color, size and/or shape. This is particularly the case when part 14a forms a measurement module including sensors 12, as in the example shown. Part 14b is then customizable by its owner or the person who wears it.

Each of parts 14a, 14b or support 14 in general comprises or is formed of an elongated strip of substantially thin and wide material. Each part 14a, 14b or support 14 has a thickness E1, E2, E (E=E1+E2) less than the width L1 of the support or device. Preferably 2*(E1 or E2 or E)<L1<4*(E1 or E2 or E), or even 2*(E1 or E2 or E)<L1<3*(E1 or E2 or E).

Parts 14a, 14b, and in particular part 14b, can be flexible by spacing their longitudinal ends, so as to facilitate the installation of the support on the individual's head. The support and its parts are for example made of plastic material and/or fabric and/or leather.

To optimize the operation of sensors and/or transmitters 12, a pressure must be applied to said sensors and/or transmitters 12 that is perpendicular to the surface of the user's head, and not perpendicular to the surface of the accessory 20 used. If the accessory 20 used follows the shape of the user's head, this constraint is not a problem. However, in the case where the accessory 20 has its own shape, independent of the shape of the user's head, this can become a problem.

Thus, according to a second embodiment illustrated in FIGS. 5a and 5b, the support 14 has the same elongated and C or U curved shape as in the previous embodiment, but support 14 may include, between parts 14a and 14b, several sheets 15, so as to have an overall bellows or accordion structure. Indeed, depending on the accessory 20 chosen by the user, the accessory 20 may not exert a homogeneous pressure on the device 10, and induce a loss of efficiency of the sensors and/or transmitters 12. In particular, if the accessory 20 is an audio headset with a hoop 18: this accessory 20 is stable on the head, widely accepted in society, in very diverse contexts, and includes in particular electronic components that can be shared with the device 10. The audio headset is therefore a very relevant accessory 20 to be used as a support for the device 10 according to the invention. However, the audio headset has a specific shape in a classic and well-known way: it does not simply rest on the top of the user's head but is also held in place by the "pinch" pressure that the headset hoop 18 exerts on the ears of the individual wearing it. This characteristic typically results in the hoop 18 not being in uniform contact with the scalp of the individual who wears it: conventionally, only the top of the hoop 18 touches the user's head, as shown in FIG. 6b. The hoop 18 therefore encloses earphones 22 from the outside to ensure pressure on the user's ears. Since the distance between the outside of the earphones placed on the ears is strictly greater than the distance between the user's ears, the radius of curvature of the hoop 18 is greater than that of the user's head (see FIG. 6b). Due to these different radii of curvature, the hoop 18 does not follow the shape of the head, it deviates from it over a significant portion (especially while moving away from the top of the head), and the surface of the hoop 18 is therefore not in continuous and uniform contact with the user's head. The second embodiment of the device 10 thus makes it possible to ensure an optimal contact and an adapted pressure for all the sensors and/or transmitters 12, and also guarantees the comfort and stability of use of the device 10.

Thus, this second embodiment of the support 14 makes it possible to adapt the distance between the sensors and/or transmitters 12 and the head, and if necessary, to ensure that the pressure exerted on each of the sensors and/or transmitters 12 on the stimulation or measurement area is adequate. Indeed, part 14b (upper side) remains in contact with the accessory 20 following its curvature (see FIG. 6a), while part 14a (lower side) follows the curvature of the user's head (see FIG. 6b). The accordion shape of support 14 allows the device 10 to push in both directions: towards accessory 20 and towards the user's head.

In addition, the support 14 according to the second embodiment has two positions. A so-called closed position (see FIG. 5a), in which parts 14a and 14b are in contact over their entire length and an open position (see FIG. 5b), in which the longitudinal ends of parts 14a and 14b are spaced from each other. The closed position makes it easier to store and transport the device 10. The closed position gives the support the same characteristics and properties as the first embodiment of the device 10.

In this second embodiment, the device 10 is electronically autonomous: it contains all the electrodes 27 necessary for its proper functioning but it is nevertheless necessary to attach an accessory 20, for example, of the audio headset type so that it functions optimally by being kept in contact with a user's head.

In this embodiment, the device can take the form of a flexible strip following any curvature without any overall elastic return force.

According to a third embodiment, close to the second embodiment, support 14 includes of two layers of leather 14a, 14b superposed, of different lengths, attached one to the other by their respective centers. As shown in FIG. 7a, part 14a (bottom face) is a strap (e.g. in leather) thick enough to carry sensors and/or transmitters 12 (here three, equally distributed over the length of the strap), intended to come into contact with the user's scalp. It is also intended to be folded over itself so as to form a loop flexible enough to fit the contour of the user's skull shape but rigid enough to act as a spring and provide the desired pressure. To that end, the part 14b (upper face) includes means for fixing each of the ends of part 14a in order to be able to maintain part 14a in its folded (or closed) position. In the example shown in FIG. 8, the attaching means of part 14b take the form of a sleeve to receive the ends of part 14a. Thus, when in the folded position and worn by the user (see FIG. 7b), support 14 according to this embodiment has the same elastic properties as the embodiment presented previously. It thus ensures, in the same way, optimal contact between the sensors and/or transmitters 12 and the surface of the user's scalp by applying a suitable pressure between the accessory 20 (here a headset hoop 18 indicated in dotted lines in FIG. 7b) and all the sensors and/or transmitters 12. This optimizes the operation of the device 10 and ensures a better user comfort. As with the previous embodiment, the rest (or open) position makes it easier in particular to store and transport the device 10. The open position gives the support 14 according to this third embodiment, the same characteristics and properties as the first embodiment of the device 10.

In the third embodiment, the device 10 is electronically autonomous but at least one of the electrodes 27 is integrated in the accessory 20, so it is necessary that the device 10 is attached and connected to the accessory 20 so that it can retrieve the signal from electrodes 27 and operate.

Figure 10B:

In general, the solution chosen to fill the gap between the user's scalp surface and the accessory 20 preferably has a flexibility that allows a certain elastic pressure to be applied to the sensors and/or transmitters 12 while allowing a so-called flat closure (or opening) of the support 14 adapted in particular to the storage of the device 10. The attaching means 16 are intended to secure the device to the accessory 20, for example to ensure optimal positioning of the device 10 on the head or to maintain it discreetly between the accessory 20 and the individual's head, especially when the accessory 20 is an audio headset, as shown in FIGS. 10a and 10b.

Attaching means 16 can be of any type. In the example shown in FIGS. 1 to 4, they include a loop extending substantially in a median plane P1 which is a median transverse plane of symmetry of the device. P2 is a median longitudinal plane of symmetry of the device 10. The loop thus defines a passage leading to the two longitudinal ends of the support 14.

The accessory 20 is intended to pass through this passage. In the case of the audio headsets in FIGS. 10a and 10b, it is the hoop 18 of the headsets that passes through the passage of the loop of the attaching means 16. The audio headsets 22 or speakers at the ends of the hoop 18 and are of the supra-aural type.

In practice, the loop can be made by attaching two elements 16a, 16b of elongated shape. A first element 16a at a first end connected to the support 14, for example at the front (zone A), and an opposite second end which is intended to be removably attached by clip-fastening or elastic clipping, by loop/hook system (of the Velcro® type for example), by magnet, by adjustable hook, by pressure, by anti-slip system, by elastic system, etc. on a first end of a second element 16b whose opposite second end is connected to the support 14, for example in the rear (zone B).

In the embodiment presented in FIGS. 9a and 9b, the attaching means 16 are in two parts: a first part 16a attached to the support 14 and at least a corresponding second part 16*b* intended to be attached to the support 14. Each part to be attached 16*b* is attached to the accessory 20, an audio headset in this case. In the example in FIGS. 5*a* and 5*b*, the attaching means 16 are magnetic and the corresponding parts 16*a* and 16*b* cooperate by magnetization. Thus, each part to be attached 16*b* is in the form of a metal clip designed to be clipped onto the hoop 18 of the audio headset. Each part to be attached 16*b* is adaptable to several thicknesses. The attaching of each part to be attached 16*b* on the hoop 18 of the audio headset allows magnetic cooperation with each corresponding attached part 16*a*, and thus allows the device 10 to be removably attached on the accessory 20.

In this example, the device 10 is an EEG measuring device 10 and has a support 14 in the form of a flexible leather strap. The support 14 carries the three attached parts 16*a* on its outer face. Each attached part 16*a* is presented in the form of a housing. The first housing 16*a* is located in the center of support 14. Two other housings 16*a* are located on either side of the first housing 16*a*, the three housings being evenly distributed on the support 14. Each housing 16*a* is surmounted by a magnet that comes opposite a corresponding clip 16*b* attached to the accessory 20.

In the examples shown, the device 10 has two sensors 12 but it could include more. It may also include transmitters. The device 10 can include two different types of sensors: measurement sensors 12, as shown in FIG. 1, for example, and also so-called mass or reference sensors (not shown in the figures).

These sensors 12 are carried by the support and in particular by its internal part 14*a*. They are substantially located at 60° of each other and at 60° of the longitudinal ends of the support 14. They are located at the level of the above-mentioned P2 plane.

Figure 11A:
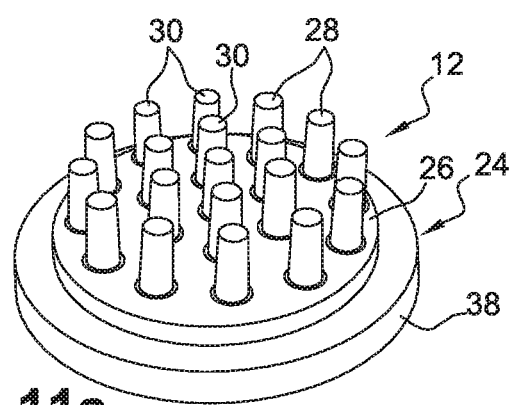
FIGS. 11a and 11b are schematic views in perspective, and in axial section for FIG. 11b, of a sensor of the device in FIG. 1.
Figure 11B:
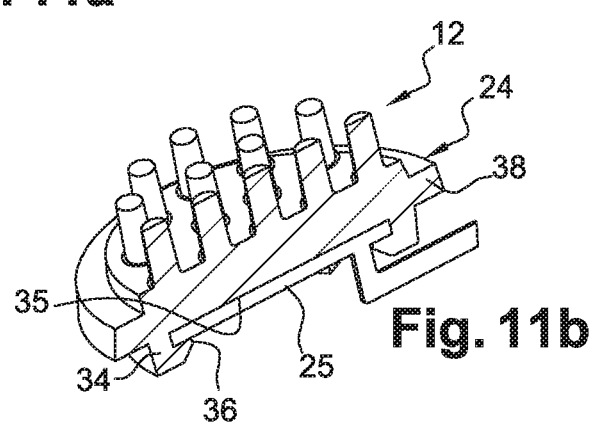
Figure 11C:
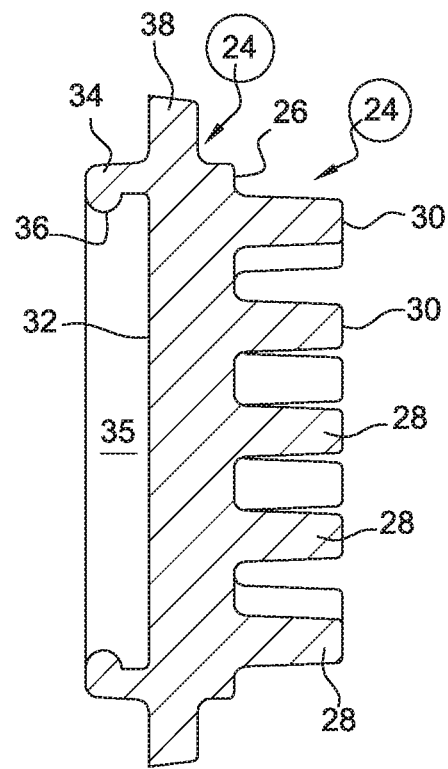

FIGS. 11*a* 11*c* represent an embodiment of the sensors 12. Each sensor 12 includes two parts, a pin 24 and an electronic board 25 for amplifying the electrical signals transmitted by the brain of the individual wearing the device 10. The amplification electronic board 25 is a small local amplification circuit (in the example considered, it is a mini round electronic board) that makes each sensor 12 "active", i.e. the signal is amplified locally, making the signal less sensitive to surrounding electromagnetic disturbances.

The pin 24 includes a disc-shaped base with one face F intended to face the individual's head and an electrode 27 consisting of a set of protruding pimples 28. Each pin 24 is made of a conductive polymeric material, preferably soft or flexible, this flexibility helping to maintain contact and pressure on the sensors and/or transmitters 12. In order to optimize this pressure, it is possible to mount the pins 24 on flexible supports (e.g. foam) of increasing size while moving away from the top of the user's head (not shown). It is also possible, for example, to mount the pins 24 on "fireplace bellows" shaped supports that can be opened or completely closed flat, potentially chained in a cascade over each other.

The pimples 28 have a general cylindrical or elongated truncated cone shape. They extend parallel to each other and perpendicular to the plane of the base. Their number is between 5 and 50 and for example between 10 and 30. Each pimple 28 has at its free end, opposite the base, at least one substantially flat circular surface 30 intended to come into contact with the scalp for the detection of brain activity. Alternatively, each pimple 28 could have a pointed end, so as to facilitate contact with the scalp.

The electrode 27 is preferably of the dry type, i.e. it is intended to come into contact with the scalp and detect electrical signals on its own, without adding any coupling liquid or gel.

In the particular example of embodiment of the invention in question, each pimple 28 of the electrode 27 has a length or height between 2 and 5 mm. Its circular free surface 30 has for example a diameter of between 1 and 2 mm.

In the example shown, the other face 32 of the pin 24 has a cylindrical flange 34 that extends about the axis X of the pin and includes a radially inner annular bead 36 with respect to that axis. This flange 34 delimits with the face 32 a recess 35 for receiving the electronic board 26, which is intended to be maintain in this recess by the bead 36 (FIGS. 6*b* and 6*c*).

The pin 24 further comprises a radially outer annular flange 38 which can be used to mount the sensor 12 in a suitable recess on the support or its part 14*a*.

The pin 24 is preferably made of a single piece of plastic material, which is advantageously relatively flexible, so that
    the electrodes 27 are flexible to facilitate contact of each free end with the individual's scalp,
    the pin 24 can be mounted by elastic clipping or slight elastic deformation in the recess of the support 14 mentioned above,
    the electronic board 25 can be engaged in the recess 35 by elastic clipping or slight elastic deformation of the bead 36 and the edge 34.

In a particular example of the embodiment of the invention, the pin 24 or the sensor has a height between 7 and 10 mm for example. Its (maximum) external diameter is for example between 10 and 30 mm.

The electrodes 27 can be made of an electrically conductive elastomeric material. They can be made from silicones loaded with conductive elements. These conductive elements include for example carbon (in the form of nanotubes for example), metal fibers, etc.

The face 32 of each sensor 12 can be slightly curved. Each local amplifier board 25 has an upper face on which electronic components are welded and a lower face (covered with a copper layer) which is pressed against the silicone by pressure thanks to the bead 36.

As mentioned above, the device 10 includes, in addition to the local amplification boards 25 at each sensor 12, a main acquisition board 26. The main acquisition board 26 is larger in size and has a higher amplification gain (in the order of x12 or even x24) than the local amplification boards 25. The acquisition board 26 may also include radio transmission tools, calculation tools, data storage means, input channels connected to the pimples 28 of each electrode 27 for the acquisition of electrical signals, means for amplifying electrical signals, wireless communication means, for example of the BLE (Bluetooth low energy) type, microprocessors or microcontrollers in particular programmable, which may, for example, allow the connection of the device to a communication device, in particular a mobile device such as a tablet or mobile phone. This can allow real-time analysis and/or processing.

The amplification board 25 of each sensor 12 is connected to the main acquisition card 26. In a variant, the amplifier boards 25 of the sensors 12 can be connected to power supply means such as a battery or rechargeable battery. The sensors 12 can be connected to the main acquisition board 26 or these power supply means (not shown) by flexible sheets of conductive wires, which extend for example inside the part 14*a* of the support 14. The main acquisition board 26 is connected to power supply means (not shown), such as a battery, for example.

As mentioned above, the device 10 may include a mass sensor.

Classically, the mass of a clinical EEG is either on the earlobe, on the nose bone, or on the mastoid bone (hard part behind the ear): all these parts have in common that they are not areas generating potential differences neither muscular, nor nervous, etc.

For example, the device 10 may include a mass sensor in the form of an ear clip (not shown). This mass sensor then has the shape of an ear clip (or loop), intended to clip onto the earlobe of the user's ear.

In the example shown in FIGS. 9a and 9b, the first central housing 16a is slightly larger than the other two and includes the mass sensor, the main electronic board 26 and the battery. The other two housings 16a, contain the measuring electrodes 12 (which pass through the strap).

In another example of embodiment (not shown), the device 10 may include a mass sensor in the form of one of the electrodes 27, for example central (inactive in this case), or electrodes 27 at the end of the support 14 intended to rest on the user's mastoids.

In another embodiment of hemoencephalography, the device 10 may include NIRS type sensors 12 to measure
the hemoglobin concentration, and/or
the oximetry, and/or
the pulse of the individual.

The measurement of hemoglobin concentration and oximetry are local measurements that provide information on brain activity in the individual's cortical region covered by the sensor 12.

In another embodiment, the device 10 may include magnetometer-type sensors 12 (e.g. CSAM) to measure the magnetic fields generated by the brain electrical activity of the individual wearing the device 10 and detect, for example, the amplitude of the alpha rhythm (brain rhythm of an alert person, eyes closed, relaxed). This embodiment can be used for neurological feedback purposes (neurofeedback).

In another embodiment, the device 10 may include thermistor-type sensors 12 to monitor the user's brain temperature and, for example, to report circadian rhythms.

In another embodiment, the device 10 may include electrical stimulation electrodes to modulate the natural electrical activity of neurons in the user's cortex. The currents generated are alternating currents and their frequency can be included in:
a frequency range conventionally measured by EEG (0.1 to 80 Hz), or
a higher frequency range (up to 5 kHz) to obtain cognitive effects,
a higher frequency range (up to 200 kHz) for therapeutic effects in the case of tumors.

Stimulation typically lasts about 10 minutes in frontal, central (e.g. Cz), parietal or occipital areas. The current intensity can typically be between 0.4 and 1 mA and in phase with natural brain oscillations at the frequency and location concerned.

In another embodiment, the device 10 may include laser or light emitting diode transducers to perform photobiomodulation of the user's brain activity.

In another embodiment, the device 10 may include conductive coils through which a current flows and generating a magnetic field directed towards the user's brain. This magnetic field induces a current in the neurons of the cortex it reaches. The coils are connected to a current pulse generator, comprising a battery coupled to a capacitance capable of reaching a sufficient voltage (in the kV range) to generate an adequate stimulation pulse.

In another embodiment, the device 10 may include ultrasonic transducers of the piezoelectric or CMUT (Capacitive micro machined ultrasonic transducers) type, generating low intensity low frequency ultrasonic waves and directed towards the user's brain to modulate its activity.

In another embodiment, the device 10 may include a combination of different transmitting and/or detecting means 12 (sensors or transmitters) mentioned above, in particular, EEG sensors 12 coupled with photobiomodulation LED transmitters 12, or NIRS sensors 12 coupled with electrical stimulation electrodes 27.

The invention claimed is:

1. A device for measuring and/or stimulating a brain activity, comprising:
means for transmitting and/or detecting physiological signals produced by a brain of an individual; and
a support for said transmitting and/or detecting means, said support being configured to extend over the top of a head of the individual, the support comprising means for removably attaching to an accessory to be worn by the head of the individual, the support being configured so that the transmitting and/or detecting means are, when the device is disposed on the head of the individual, interposed between the accessory and the head of the individual, and maintained in substantially tight contact on the head of the individual,
and wherein the support is configured to deform between a first position wherein the support is flat and a second position wherein the support is curved in order to adapt the shape of the accessory to the head of the individual,
wherein the means for transmitting and/or detecting physiological signals comprise measurement sensors, a mass sensor and a reference sensor which are carried by the support,
wherein each measurement sensor comprises a pin which includes an electrode and an electronic board for amplifying the electrical signals detected by the means for transmitting and/or detecting physiological signals, the electronic board being located in a recess delimited by a cylindrical flange extending about an axis of the pin.

2. The device according to claim 1, wherein said attaching means forms a loop to enclose said accessory or be traversed by said accessory.

3. The device according to claim 1, wherein said attaching means are selected from a group consisting of magnets, hooks and loops, shape cooperation, elastic clipping, anti-slip elements and elastic elements.

4. The device according to claim 1 wherein the electrode is a dry electrode configured to come into contact with the scalp of the individual wearing the device, without the use of coupling fluid.

5. The device according to claim 1, wherein the pins are made of a conductive polymer material.

6. The device according to claim 1, wherein the electric board is configured for processing said signals.

7. The device according to claim 1, further comprising means for remote communication with an electronic system independent of said accessory.

8. An audio headset, comprising:
a hoop carrying two opposite ends of a means for transmitting sounds or music, comprising at least one device according to claim 1 removably attached to the support.

9. The device according to claim 1, wherein the device is an EEG device.

10. A device for measuring and/or stimulating a brain activity, comprising:

a plurality of sensors comprising measurement sensors, a mass sensor and a reference sensor;

a support configured to support the plurality of sensors, said support being configured to extend over the top of a head of the individual;

an attachment coupled to the support, the attachment configured for removable attachment to an accessory to be worn by the head of the individual, the support being configured so that the plurality of sensors are, when the device is disposed on the head of the individual, interposed between the accessory and the head of the individual, and maintained in substantially tight contact on the head of the individual, wherein the support is configured to deform between a first position wherein the support is flat and a second position wherein the support is curved in order to adapt the shape of the accessory to the head of the individual, wherein each measurement sensor comprises a pin which includes an electrode and an electronic board for amplifying electrical signals detected by the electrode, the electronic board being located in a recess delimited by a cylindrical flange extending about an axis of the pin.

11. The device of claim 10, wherein the attachment is selected from a group consisting of magnets, hooks and loops, shape cooperation, elastic clipping, anti-slip elements and elastic elements.

12. The device according to claim 1, wherein the support is formed of an elongated strip being configured to be interposed between the accessory and the head of the individual, the strip having a thickness and a width, the thickness being inferior than the width.

13. The device according to claim 12, wherein the width is superior than twice the thickness and inferior than four times the thickness.

14. The device according to claim 12, wherein the strip has no elastic return force.

15. The device according to claim 13, wherein the strip has no elastic return force.

16. The device according to claim 1, wherein the support comprises a first part and a second part, the means for transmitting and/or detecting physiological signals being fixed on the second part, and sheets arranged between the first and second parts, and wherein in the first position the first and second parts are in contact over their entire length through the sheets, and in the second position, longitudinal ends of the first and second parts are spaced from each other so as the second part is curved.

17. The device according to claim 1, wherein the support comprises a first part and a second part, the means for transmitting and/or detecting physiological signals being fixed on the second part, the first and second part having different lengths and being attached one to the other, and wherein in the second position ends of the second part are folded and fixed to the first part so as to have a loop shape, and in the first position the second part is unfolded so to obtain a flat support.

18. The device according to claim 1, wherein the cylindrical flange includes a radially inner annular bead with respect to the axis of the pin and that maintains the electronic board in the recess.

19. The device according to claim 1, wherein the device further comprises a main acquisition board connected to the amplification board of each sensor and a battery, the main acquisition board being located in the support.

20. The device according to claim 18, wherein the device further comprises a main acquisition board connected to the amplification board of each sensor and a battery, the main acquisition board being located in the support.

21. The device according to claim 1, wherein the means for transmitting and detecting physiological signals comprise stimulation electrodes.

22. The device according to claim 1, wherein the means for transmitting and/or detecting physiological signals are embedded in a recess managed on the support.

23. A device for measuring and/or stimulating a brain activity, comprising:

means for transmitting and/or detecting physiological signals produced by a brain of an individual; and a support for said transmitting and/or detecting means, said support being configured to extend over the top of a head of the individual, the support comprising means for removably attaching to an accessory to be worn by the head of the individual, the support being configured so that the transmitting and/or detecting means are, when the device is disposed on the head of the individual, interposed between the accessory and the head of the individual, and maintained in substantially tight contact on the head of the individual, wherein the support is configured to deform between a first position wherein the support is flat and a second position wherein the support is curved in order to adapt the shape of the accessory to the head of the individual, wherein the support comprises a first part and a second part, the means for transmitting and/or detecting physiological signals being fixed on the second part, and sheets arranged between the first and second parts, wherein in the first position the first and second parts are in contact over their entire length through the sheets, and in the second position, longitudinal ends of the first and second parts are spaced from each other so as the second part is curved.

24. A device for measuring and/or stimulating a brain activity, comprising:

means for transmitting and/or detecting physiological signals produced by a brain of an individual; and a support for said transmitting and/or detecting means, said support being configured to extend over the top of a head of the individual, the support comprising means for removably attaching to an accessory to be worn by the head of the individual, the support being configured so that the transmitting and/or detecting means are, when the device is disposed on the head of the individual, interposed between the accessory and the head of the individual, and maintained in substantially tight contact on the head of the individual, wherein the support is configured to deform between a first position wherein the support is flat and a second position wherein the support is curved in order to adapt the shape of the accessory to the head of the individual, wherein the support comprises a first part and a second part, the means for transmitting and/or detecting physiological signals being fixed on the second part, the first and second part having different lengths and being attached one to the other, wherein in the second position, ends of the second part are folded and fixed to the first part so as to have a loop shape, and in the first position the second part is unfolded so to obtain a flat support.

* * * * *